US010161891B1

(12) United States Patent
Tian et al.

(10) Patent No.: US 10,161,891 B1
(45) Date of Patent: Dec. 25, 2018

(54) METHOD FOR CHARACTERIZING ROCK PHYSICAL CHARACTERISTICS OF DEEPLY BURIED CARBONATE ROCKS

(71) Applicant: INSTITUTE OF GEOLOGY AND GEOPHYSICS CHINESE ACADEMY OF SCIENCES, Beijing (CN)

(72) Inventors: Fei Tian, Beijing (CN); Xu Xue, Beijing (CN); Naigui Liu, Beijing (CN); Changchun Yang, Beijing (CN)

(73) Assignee: INSTITUTE OF GEOLOGY AND GEOPHYSICS CHINESE ACADEMY OF SCIENCES, Beijing (CN)

(*) Notice: Subject to any disclaimer, the term of this patent is extended or adjusted under 35 U.S.C. 154(b) by 0 days.

(21) Appl. No.: 15/984,430

(22) Filed: May 21, 2018

(30) Foreign Application Priority Data

Nov. 3, 2017 (CN) .......................... 2017 1 1076066

(51) Int. Cl.
*G01N 24/08* (2006.01)
*E21B 49/02* (2006.01)
(Continued)

(52) U.S. Cl.
CPC ........... *G01N 24/081* (2013.01); *E21B 49/02* (2013.01); *G01N 1/08* (2013.01); *G01V 3/14* (2013.01)

(58) Field of Classification Search
CPC ........ G01N 24/081; G01N 1/08; E21B 49/02; G01V 3/14
(Continued)

(56) References Cited

U.S. PATENT DOCUMENTS

2005/0256643 A1* 11/2005 Boitnott ................. G01V 11/00
702/6
2007/0276639 A1* 11/2007 Montaron .............. G01V 11/00
703/10
(Continued)

OTHER PUBLICATIONS

Aaron J. Adams, "Relationships Between Observed Pore and Pore-Throat Geometries, Measured Porosity and Permeability, and Indirect Measures of Pore Volume by Nuclear Magnetic Resonance", Dec. 31, 2005; Texas A&M University.
(Continued)

*Primary Examiner* — Melissa J Koval
*Assistant Examiner* — Rahul Maini
(74) *Attorney, Agent, or Firm* — Platinum Intellectual Property LLP

(57) ABSTRACT

The invention relates to the technical field of oilfield exploration and development, and particularly relates to a method for characterizing the rock physical characteristics of deeply buried carbonate rocks, comprising the following steps: determining a rock type of a rock thin section by identifying the surface structure characteristics of the rock thin section corresponding to a core plunger sample; performing a normal pressure nuclear magnetic resonance test and rock physical characteristic tests on the core plunger sample; establishing an identification plate, a first relation, a second relation and a third relation; characterizing the rock physical characteristics of a target rock sample under normal pressure and its buried depth according to the normal pressure nuclear magnetic resonance test result and the overburden pressure nuclear magnetic resonance test result of the target rock sample respectively.

10 Claims, 1 Drawing Sheet

(51) Int. Cl.
*G01N 1/08* (2006.01)
*G01V 3/14* (2006.01)

(58) Field of Classification Search
USPC .......................................................... 324/309
See application file for complete search history.

(56) References Cited

U.S. PATENT DOCUMENTS

2016/0187532 A1* 6/2016 Hurley ................. G01V 11/002
  702/12
2018/0259467 A1* 9/2018 Buono ..................... G01V 3/32

OTHER PUBLICATIONS

Lawrence M. Anovitz, David R. Cole, "Characterization and Analysis of Porosity and Pore Structures"; Reviews in Mineralogy & Geochemistry; vol. 80 pp. 61-164, 2015; Mineralogical Society of America.

Qibin Yan, Hui Zhao, Liqiang Sima , Zhenfei Shi; "A Study of NMR Experiments of Carbonates"; Nov. 16, 2009; China.

Zhizhan Wang, Yardenia Martinez, Kurt Strack, Gang Yu; "Applications of NMR Mud Logging Technology in China"; SPWLA 48th Annual Logging Symposium, Jun. 3-6, 2007; Houston, USA.

Qibin Yan, Hui Zhao, Liqiang Sima, Zhenfei Shi; "A Study of Nmr Experiments of Carbonates", Natural Gas Industry, vol. 30, Issue 1, pp. 36-38, Jan. 25, 2010; ISSN 1000-0976, China.

* cited by examiner

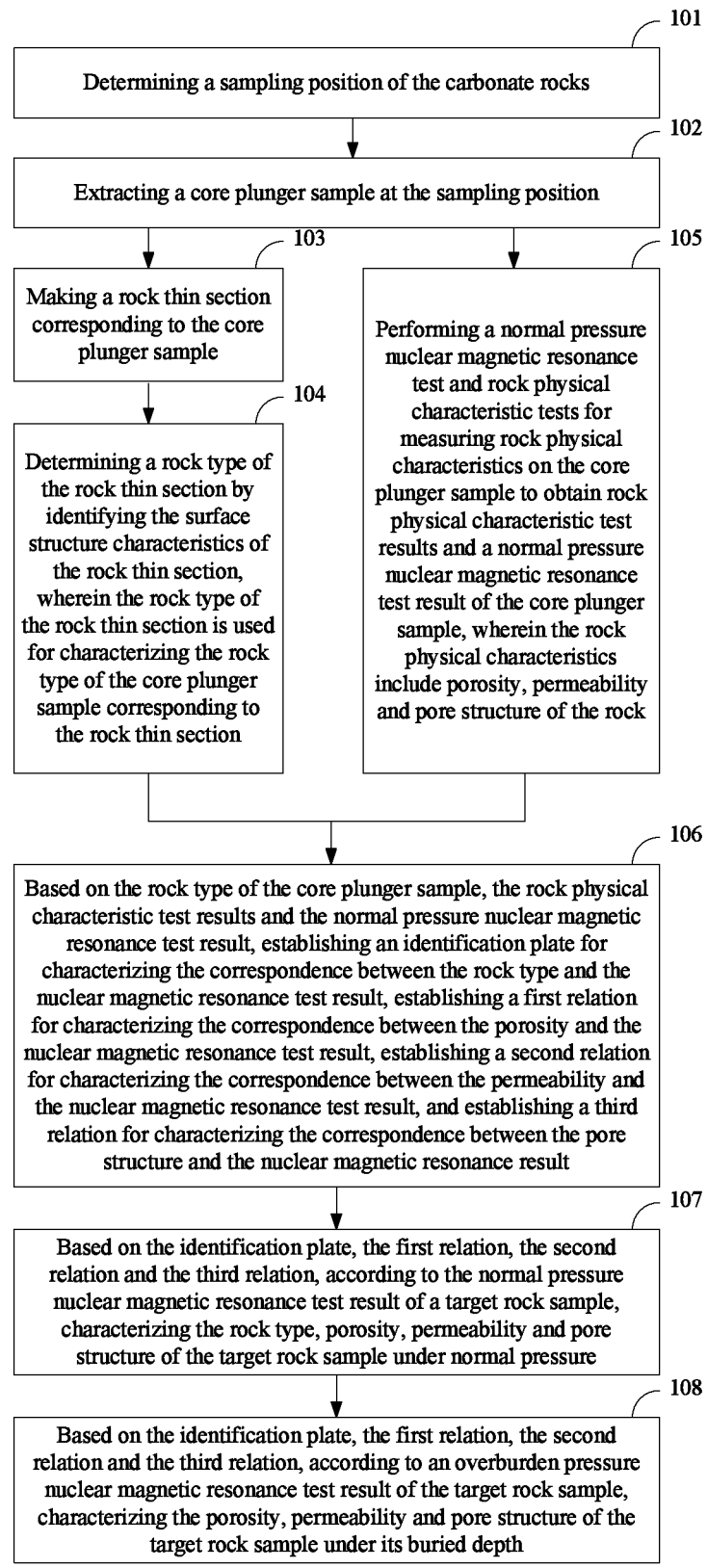

METHOD FOR CHARACTERIZING ROCK PHYSICAL CHARACTERISTICS OF DEEPLY BURIED CARBONATE ROCKS

RELATED APPLICATIONS

This application is a Non-provisional Application under 35 USC 111(a), which claims Chinese Patent Application Serial No. 201711076066.9, filed Nov. 3, 2017, the disclosure of all of which are hereby incorporated by reference in their entirety.

FIELD OF THE INVENTION

The present invention relates to the technical field of oilfield exploration and development, and particularly relates to a method for characterizing the rock physical characteristics of deeply buried carbonate rocks.

BACKGROUND OF THE INVENTION

In the process of oil and gas exploration and development, the oil and gas industry needs to accurately characterize the rock physical characteristics of underground reservoirs, so as to evaluate the storage capabilities of the underground reservoirs, judge the economic values of the underground reservoirs, determine the exploration and development strategies of the underground reservoirs, and improve the accuracy and economic benefits of the oil and gas exploration. The rock physical characteristics mainly include porosity, permeability, and pore structure. Therefore, it has a great guiding significance for the oil and gas exploration and development to accurately characterize the rock physical characteristics of reservoirs.

Carbonate reservoirs are one of the main oil and gas reservoirs, and the carbonate reservoirs having rock components easily affected by later diagnoses are complex in storage space and diverse in pore structure. Therefore, it is very difficult to effectively characterize the rock physical characteristics of the carbonate reservoirs. With continuous improvements on the oil and gas exploration technology, deeply buried carbonate oil and gas reservoirs having the buried depths of more than 4500 meters have received more and more attentions. Compared with medium-shallow reservoirs having the buried depths of less than 4500 meters, the deeply buried carbonate reservoirs have the characteristics of deep burial depth, low porosity and permeability and more complex pore structure. Therefore, it is quite difficult to effectively characterize the rock physical characteristics of the deeply buried carbonate reservoirs.

In terms of how to accurately characterize the rock physical characteristics of deeply buried carbonate reservoirs, the traditional methods for characterizing the rock physical characteristics of a medium-shallow reservoir are usually adopted in the prior art. For example, the rock physical characteristics are characterized by measuring the core characteristics of a cored segment, including observing thin sections to qualitatively describe the pore structure, semi-quantitatively analyzing the pore morphology and chemical components via a scanning electron microscope, or quantitatively obtaining micro-scale CT slices via high-precision CT scanning experiments to reconstruct a three-dimensional microscopic pore structure. However, since the deeply buried carbonate rocks have quite complex pore structure and extremely strong heterogeneity, the traditional methods cannot accurately characterize the rock physical characteristics of the deeply buried carbonate rocks, and then the developmental characteristics of the deeply buried carbonate reservoirs cannot be accurately evaluated.

SUMMARY OF THE INVENTION

In view of the above problems, the present invention provides a method for characterizing the rock physical characteristics of deeply buried carbonate rocks for overcoming the above problems or at least partially solving the above problems.

An embodiment of the present invention provides a method for characterizing the rock physical characteristics of deeply buried carbonate rocks, including the following steps:

determining a sampling position of the carbonate rocks;
extracting a core plunger sample at the sampling position;
making a rock thin section corresponding to the core plunger sample;
determining a rock type of the rock thin section by identifying the surface structure characteristics of the rock thin section, wherein the rock type of the rock thin section is used for characterizing the rock type of the core plunger sample corresponding to the rock thin section;
performing a normal pressure nuclear magnetic resonance test and rock physical characteristic tests for measuring rock physical characteristics on the core plunger sample to obtain rock physical characteristic test results and a normal pressure nuclear magnetic resonance test result of the core plunger sample, wherein the rock physical characteristics include porosity, permeability and pore structure of rock;
based on the rock type of the core plunger sample, the rock physical characteristic test results and the normal pressure nuclear magnetic resonance test result, establishing an identification plate for characterizing the correspondence between the rock type and the nuclear magnetic resonance test result, establishing a first relation for characterizing the correspondence between the porosity and the nuclear magnetic resonance test result, establishing a second relation for characterizing the correspondence between the permeability and the nuclear magnetic resonance test result, and establishing a third relation for characterizing the correspondence between the pore structure and the nuclear magnetic resonance result;
based on the identification plate, the first relation, the second relation and the third relation, according to the normal pressure nuclear magnetic resonance test result of a target rock sample, characterizing the rock type, porosity, permeability and pore structure of the target rock sample under normal pressure; and
based on the identification plate, the first relation, the second relation and the third relation, according to an overburden pressure nuclear magnetic resonance test result of the target rock sample, characterizing the porosity, permeability and pore structure of the target rock sample under its buried depth.

Preferably, the sampling position includes a carbonate segment without vugs and caves developing, a semi-filled crack developed segment and a full-filing crack developed segment, the rock type of the sampling position is uniform, and the rock thickness of the sampling position is more than 30 cm.

Preferably, the height of the core plunger sample is 3.0-6.0 cm.

Preferably, the surface structure characteristics comprise at least one of carbonate grain characteristic, carbonate mud characteristic, biological framework characteristic, carbonate crystalline characteristic and crack characteristic, and the rock type is mudstone, wackestone, packstone, grainstone, boundstone, crystalline carbonates, semi-filled crack carbonate rock or full-filled crack carbonate rock.

Preferably, the step of performing rock physical characteristic tests on the core plunger sample include:
performing a porosity test, a permeability test and a mercury-injection capillary pressure test on the core plunger sample.

Preferably, before the step of characterizing the porosity, permeability and pore structure of the target rock sample under its buried depth, the method further includes the following step:

Performing an overburden pressure nuclear magnetic resonance test on the target rock sample to obtain an overburden pressure nuclear magnetic resonance test result of the target rock sample;
wherein the step of performing an overburden pressure nuclear magnetic resonance test on the target rock sample includes:

Performing a nuclear magnetic resonance test on the target rock sample under a specified test pressure, wherein the specified test pressure is lithostatic pressure corresponding to the buried depth of the target rock sample.

Preferably, the step of establishing an identification plate for characterizing the correspondence between the rock type and the nuclear magnetic resonance test result includes:
dividing the pores of the core plunger sample according to the length of relaxation time in the normal pressure nuclear magnetic resonance test result, wherein the normal pressure nuclear magnetic resonance spectra having a relaxation time of more than 200 ms in the normal pressure nuclear magnetic resonance test result are divided into large pores of the core plunger sample, the normal pressure nuclear magnetic resonance spectra having a relaxation time of more than 20 ms and less than 200 ms in the normal pressure nuclear magnetic resonance test result are divided into medium pores of the core plunger sample, and the normal pressure nuclear magnetic resonance spectra having a relaxation time of less than 20 ms in the normal pressure nuclear magnetic resonance test result are divided into small pores of the core plunger sample;
respectively calculating the percentages of the normal pressure nuclear magnetic resonance spectrum areas corresponding to the large pores, the medium pores and the small pores to the total area of the normal pressure nuclear magnetic resonance spectrum; and
respectively projecting the percentage of the normal pressure nuclear magnetic resonance spectrum area corresponding to the large pores to the total area of the normal pressure nuclear magnetic resonance spectrum, the percentage of the normal pressure nuclear magnetic resonance spectrum area corresponding to the medium pores to the total area of the normal pressure nuclear magnetic resonance spectrum and the percentage of the normal pressure nuclear magnetic resonance spectrum area corresponding to the small pores to the total area of the normal pressure nuclear magnetic resonance spectrum to a triangular plot plate to obtain the identification plate.

Preferably, the first relation is:

$$\Phi_{nmr} = C_\Phi \times \frac{A}{V_b} \times 100\%$$

wherein $\Phi_{nmr}$ is the porosity of the core plunger sample, $V_b$ is the volume of the core plunger sample, A is the total amplitude of nuclear magnetic resonance test echo signals, and $C_\Phi$ is a scale factor between the porosity measured from a standard sample having known porosity and the porosity of nuclear magnetic resonance calculation.

Preferably, the second relation is:

$$K_{nmr} = C_K \times \left(\frac{\Phi_{nmr}}{100}\right)^4 \times T_{2g}^2$$

wherein $K_{nmr}$ is the permeability of the core plunger sample, $C_K$ is a scale factor between the permeability measured from the standard sample having known permeability and the permeability of nuclear magnetic resonance calculation, $\Phi_{nmr}$ is the porosity of the core plunger sample, and $T_{2g}$ is a geometric mean of the nuclear magnetic resonance transverse relaxation time of the core plunger sample.

Preferably, the third relation is:

$$r_c = C_r \times T_2$$

wherein $r_c$ is the pore throat radius of the core plunger sample, $T_2$ is the nuclear magnetic resonance transverse relaxation time, and $C_r$ is a conversion coefficient between the pore structure measured from the standard sample having known pore structure and the pore structure of nuclear magnetic resonance conversion.

One or more technical solutions in the embodiments of the present invention at least have the following technical effects or advantages:

In the present application, after a core plunger sample is extracted, a rock thin section corresponding to the core plunger sample is made, and the surface structure characteristics of the rock thin section are identified to determine the rock type of the rock thin section. The rock type of the rock thin section characterizes the rock type of the core plunger sample corresponding to the rock thin section. In the present application, after the core plunger sample is extracted, a rock physical characteristic test for measuring rock physical characteristics and a normal pressure nuclear magnetic resonance test are also performed on the core plunger sample to obtain rock physical characteristic tests result and a normal pressure nuclear magnetic resonance test result of the core plunger sample. The rock physical characteristics include porosity, permeability and pore structure of the rock. Then, based on the rock type of the core plunger sample, the rock physical characteristic test results and the normal pressure nuclear magnetic resonance test result, an identification plate for characterizing the correspondence between the rock type and the nuclear magnetic resonance test result is established, a first relation for characterizing the correspondence between the porosity and the nuclear magnetic resonance test result is established, a second relation for characterizing the correspondence between the permeability and the nuclear magnetic resonance test result is established, and a third relation for characterizing the correspondence between the pore structure and the nuclear magnetic resonance result is established. Further, based on the identification plate, the first relation, the second relation and the third relation, according to the normal pressure nuclear magnetic resonance test result of the target rock sample, the rock type, porosity, permeability and pore structure of the target rock sample under normal pressure are characterized, and according to an overburden pressure nuclear magnetic resonance test result of the target rock sample, the porosity, permeability and pore structure of the target rock sample under its buried depth are characterized. Therefore, the rock physical characteristics of the target rock sample under the laboratory normal pressure environment and its buried depth are obtained massively, quickly, non-destructively and accurately, and a technical support is provided for oilfield evaluation on underground rock physical characteristics of each rock type.

BRIEF DESCRIPTION OF THE DRAWING

By reading the detailed description of the following preferred embodiments, various other advantages and benefits will become clear for those of ordinary skill in the art. The accompanying drawing is merely used for showing the purposes of the preferred embodiments, rather than limiting the present invention. Moreover, in the whole drawing, the same components are represented by the same reference signs. In the drawing:

FIG. 1 shows a flow diagram of a method for characterizing the rock physical characteristics of deeply buried carbonate rocks in an embodiment of the present invention.

DETAILED DESCRIPTION OF THE EMBODIMENTS

Exemplary embodiments of the present disclosure will be described in more detail below with reference to the accompanying drawing. Although the exemplary embodiments of the present disclosure are shown in the accompanying drawing, it should be understood that the present disclosure can be realized in various forms but should not be limited by the embodiments illustrated herein. Conversely, these embodiments are provided in order to understand the present disclosure more thoroughly and completely transmit the scope of the present disclosure to those skilled in the art.

An embodiment of the present invention provides a method for characterizing the rock physical characteristics of deeply buried carbonate rocks, which is used for researching the rock physical characteristics of the deeply buried carbonate rocks having the buried depth of over 4500 meters. As shown in FIG. 1, the method includes the following steps:

Step 101: determining a sampling position of the carbonate rocks.

In the present application, the sampling position of the carbonate rocks needs to be determined first. As for step 101, in the specific implementation process, a carbonate segment without vugs and caves developing, a semi-filled crack developed segment and a full-filing crack developed segment are determined as the sampling position. Further, in consideration of heterogeneity of carbonate rocks, the rock stratum of the sampling position needs to have uniform rock type, i.e., the rock stratum of the sampling position only includes one rock type, and at the same time, the rock thickness of the sampling position is more than 30 cm.

After step 101 is completed, step 102 is executed: extracting a core plunger sample from the sampling position.

For step 102, in the specific implementation process, the sampling position is drilled with a core drill to extract the core plunger sample, then two ends of the core plunger sample are polished smooth with a core cutter, and the core plunger sample is numbered and labeled, and the label records the sampling position of the core plunger sample and the corresponding number. For example, the first core plunger sample extracted from the carbonate segment without vugs and caves developing is numbered as 1, while the label stuck to the first core plunger sample records the number "1" and the sampling position "a carbonate segment without vugs and caves developing", wherein the height of the core plunger sample is preferably 3.0-6.0 cm, and the diameter may be 2.0-3.0 cm.

After step 102 is completed, step 103 is executed: making a rock thin section corresponding to the core plunger sample.

Regarding step 103, in the specific implementation process, the remaining core sample corresponding to the core plunger sample in step 102 can be made to the rock thin section. Similarly, after the rock thin section is made, the rock thin section can also be numbered and labeled, and the label records the core plunger sample corresponding to the rock thin section. For example, the made first rock thin section corresponding to the first core plunger sample is numbered as 1, and the label stuck to the first rock thin section records the number "1" and "first core plunger sample". In the actual manufacturing process, the rock thin section has the thickness of 0.03 mm, the length of 20-40 mm, and the width of 10-30 mm. It should be noted that the thickness 0.03 mm of the rock thin section is a necessary thickness required by industry norms, and the length and width of the rock thin section can be selected within said ranges according to actual situations.

After step 103 is completed, step 104 is executed: determining a rock type of the rock thin section by identifying the surface structure characteristics of the rock thin section.

In terms of step 104, in the specific implementation process, the rock thin section can be identified by using a polarizing microscope and a microphotograph system. Further, identification on the surface structure characteristics of the rock thin section includes at least one of identification on carbonate grain characteristic, identification on carbonate mud characteristic, identification on biological framework characteristic, identification on carbonate crystalline characteristic and identification on crack characteristic, wherein the crack characteristic identification specifically includes identification on the development condition and development position of cracks. Preferably, all the said characteristics are identified for the same rock thin section. The microphotograph system can be utilized for shooting during identification, and the obtained photo is numbered and named, so that a correspondence can be established between the photo and the corresponding rock thin section.

Further, the rock type of the rock thin section can be determined based on the carbonate classification scheme of Dunham and the development and filling condition of cracks according to the obtained surface structure characteristics of the rock thin section, and the determined rock type will be recorded to the label of the rock thin section. The rock type is mudstone, wackestone, packstone, grainstone, boundstone, crystalline carbonates, semi-filled crack carbonate rock or full-filled crack carbonate rock.

Specifically, the mudstone is mainly composed of carbonate mud having a particle size of less than 30 μm, the carbonate mud is mainly formed by chemical precipitation, mechanical crushing, biological factors and the like, and the particle content is less than 10%. The wackestone is supported by carbonate mud, the plaster content is over 50%, and the particle content is over 10%. The packstone is mainly supported by carbonate grains, the grain content is over 50%, and the spaces between the grains are filled with carbonate mud. The grainstone is mainly supported by grains, the carbonate mud precipitate can be hardly viewed, the grains are mainly composed of intraclast, ooid, biological detritus and the like, and the spaces between the grains are filled with recrystallized calcite. In tight carbonate strata, the development of cracks can better improve the physical characteristics of the strata. The diagnoses such as dissolution and precipitation inside the carbonate strata happens frequently and interactively, the cracks in the strata where underground water flows relatively actively are mostly semi-filled, and such carbonate rock is referred to as the semi-filled crack carbonate rock. The diagnoses such as dissolution and precipitation inside the carbonate strata happens frequently and interactively, the cracks in the strata where underground water is in a flow stagnation state are easily filled by later calcite and the like, and such carbonate rock is referred to as the full-filled crack carbonate rock.

It should be noted that, in the present application, the rock type of the rock thin section is used for characterizing the rock type of the core plunger sample corresponding to the rock thin section, that is to say, the rock type of the rock thin section is the rock type of the core plunger sample corresponding to the rock thin section. For example, the rock type of the first rock thin section No. 1 is the rock type of the first core plunger sample No. 1.

After step 102 is completed, step 105 is further executed: performing a normal pressure nuclear magnetic resonance test and rock physical characteristic tests for measuring rock physical characteristics on the core plunger sample to obtain rock physical characteristic test results and a normal pressure nuclear magnetic resonance test result of the core plunger sample, wherein the rock physical characteristics include porosity, permeability and pore structure of the rock.

For step 105, before the rock physical characteristic tests and the normal pressure nuclear magnetic resonance test are performed on the core plunger sample, the core plunger samples need to be pretreated, wherein before the rock physical characteristic test is performed on the core plunger samples, the method further includes the following step: removing original fluid from the core plunger sample, and drying the core plunger sample; before the normal pressure nuclear magnetic resonance test is performed on the core plunger sample, the method further includes the following step: removing original fluid from the core plunger sample, drying the core plunger sample, and then saturating the core plunger sample. Specifically, the original fluid can be removed from the core plunger sample by adopting a centrifuge, a clean thermal solvent needs to be jetted to the core plunger sample when the centrifuge is running, and the solvent flows through the core plunger sample by means of a centrifugal force to displace all the original fluid in the core plunger sample. Optionally, the revolution speed of the centrifuge is 8000-14000 revolutions per minute, and the centrifugal time is 30 minutes. Next, after the fluid is removed from the core plunger sample, the core plunger sample needs to be dried, and the core plunger sample is dried to a constant weight by using a conventional oven. In addition, before the nuclear magnetic resonance test is performed on the core plunger sample and after the fluid is removed from the core plunger sample, the core plunger sample is dried and then saturated, wherein the saturated solution is a simulated stratum water solution.

Next, the process of performing the rock physical characteristic tests and the normal pressure nuclear magnetic resonance test on the core plunger sample is executed to obtain rock physical characteristic test results and a normal pressure nuclear magnetic resonance test result of the core plunger sample respectively.

After step 104 and step 105 are completed, step 106 is executed: based on the rock type of the core plunger sample, the rock physical characteristic test results and the normal pressure nuclear magnetic resonance test result, establishing an identification plate for characterizing the correspondence between the rock type and the nuclear magnetic resonance test result, establishing a first relation for characterizing the correspondence between the porosity and the nuclear magnetic resonance test result, establishing a second relation for characterizing the correspondence between the permeability and the nuclear magnetic resonance test result, and establishing a third relation for characterizing the correspondence between the pore structure and the nuclear magnetic resonance result.

The specific implementation processes of step 105 and step 106 will be specified below.

In step 105, the rock physical characteristic tests performed on the core plunger sample include a porosity test, a permeability test and a mercury-injection capillary pressure test. The porosity of the core plunger sample can be obtained via the porosity test, the permeability of the core plunger sample can be obtained via the permeability test, the pore throat distribution of the core plunger sample can be obtained via the mercury-injection capillary pressure test, and its pore structure is thus obtained.

For the porosity test, the porosity of the core plunger sample is finally obtained via the porosity test, the porosity ($\Phi$) is a ratio of the pore space volume ($V_p$) of the core plunger sample to its total volume ($V_b$), wherein the difference between the total volume ($V_b$) of the core plunger sample measured in a laboratory to the particle volume ($V_g$) is the pore volume ($V_p$), and $\Phi$ can be solved via the following formula:

$$\Phi = \frac{V_b - V_g}{V_b}.$$

further, the specific measurement processes of $V_g$ and $V_b$ of the core plunger sample are as follows:

For $V_g$, helium is used as a displacing medium, and the framework volume of the core plunger sample is measured by adopting a gas porosity measuring device under the isothermal environment. Specifically, step 1, the core plunger sample is put into a core chamber (the volume of the core chamber is known, and is $V_1$), a sample valve and an emptying valve are opened to ensure that the gas pressure of the core chamber is atmospheric pressure); step 2, the sample valve and the emptying valve are closed, and the original pressure $P_0$ (measured by a pressure gauge A) of the core chamber is recorded; step 3, a gas source valve and a gas supply valve are opened, a pressure adjusting valve is adjusted, the gas pressure of a standard chamber is adjusted to a preset pressure value (the volume of the standard chamber is known, and is $V_2$) in the range of 500-900 kPa, the gas supply valve is closed after the pressure is stable, and the gas pressure $P_1$ (measured by a pressure gauge B) of standard chamber is recorded; step 4, the sample valve is opened, the gas is expanded from the standard chamber to the rock chamber, and after the pressure is stable, the balance pressure $P_2$ (measured by the pressure gauge) is recorded; step 5, the sample valve and the emptying valve are opened so that the gas pressure of the core chamber is atmospheric pressure, and the core plunger sample is taken out; and step 6, the $V_g$ of the core plunger sample is calculated, and it can be known from the Boyle's law:

$(V_1-V_g) \times P_0 + V_2 \times P_1 = (V_1+V_2-V_g) \times P_2,$ thus, the following formula is obtained:

$$V_g = V_1 - V_2 \times \frac{P_2 - P_1}{P_2 - P_0}.$$

For $V_b$, the total volume of the core plunger sample is measured by adopting an Archimedean mercury immersion method. Specifically, step 1, the core plunger sample is enveloped by a polytetrafluoroethylene tube, wherein an air gap is forbidden between the polytetrafluoroethylene tube and the core plunger sample; step 2, in a laboratory of 25° C., the core plunger sample enveloped by the polytetrafluoroethylene tube is immersed into mercury, and the displaced mercury volume is measured; and step 3, the volume of the polytetrafluoroethylene tube is subtracted from the displaced mercury volume to obtain the total volume of the core plunger sample.

For the permeability test, the permeability of the core plunger sample is finally obtained via the permeability test, the permeability is measured according to the gas one-dimensional steady permeation Darcy law and reflects the capability of fluid flowing through the rock sample under a pressure difference, the permeability is measured by using the transmission "drop" principle in the present application, helium filled into a tank having known exact volume passes through the core plunger sample, the helium flows into air, the attenuated tank pressure is monitored with time, the gas velocity and pressure drop of the core plunger sample are measured at each given time, a computer acquires the change data of a series of inlet pressure with time, and the permeability of the core plunger sample is thus obtained.

For the mercury-injection capillary pressure test, the pore throat distribution of the core plunger sample is finally obtained via the mercury-injection capillary pressure test, wherein the pore throat distribution represents the pore structure. Only the shape, size and communicating form of pores on one plane and the pore combination type can be observed according to microscopic observation of the rock thin section and image pore analysis, but the overall pore system of the core plunger sample cannot be qualitatively and quantitatively evaluated. Meanwhile, because the pore space of the carbonate rock is extremely complex and the pore canals are tortuous, a capillary pressure curve can be obtained by the mercury-injection capillary pressure test on the core plunger sample in the present application to analyze the pore structure.

Specifically, the mercury-injection capillary pressure test can be implemented by adopting a high-pressure mercury injection method, mercury is used as a non-wetting phase in the present application and injected to a rock pore system to overcome the capillary resistance generates by pores and throats, the injection pressure and the volume of the injected mercury are recorded, and a relation between the injection pressure and the mercury saturation is obtained. The slope of the capillary pressure curve records the volume percentage of fluid entering the pores via a throat greater than a specific size under a certain capillary pressure (PC), the capillary pressure curve can reflect the throat structure of the core plunger sample and the probability distribution thereof and characterize pore structure parameters of the rock sample, e.g., pore throat mean, throat sorting coefficient, average throat radius, etc., the shape of the capillary pressure curve depends on good or bad interconnection of pores and the size distribution of pores, the capillary pressure curve can realize quantitative characterization of the pore structure, moreover, the shape of the capillary pressure curve is mainly controlled by the sorting property and size of pore throats, and the reservoir property and productivity of rock can be qualitatively judged from the mercury-injection capillary pressure test.

Specifically, the capillary pressure and the pore throat radius have the following relation:

$$P_C = \frac{2 \times \sigma \times \cos\theta}{r_C}$$

wherein $P_C$ is capillary pressure and its unit is MPa, $\sigma$ is fluid interfacial tension and its unit is N/cm2, $\theta$ is a wetting contact angle and its unit is °, $r_c$ is pore throat radius and its unit is μm. For mercury, $\sigma$=49.44 N/cm$^2$, and $\theta$=140°, so $$P_C = \frac{0.735}{r_C}.$$

In step 105, a normal pressure nuclear magnetic resonance test is performed on the core plunger sample to obtain a normal pressure nuclear magnetic resonance test result, wherein the normal pressure is an atmospheric pressure.

For the nuclear magnetic resonance test, the present application adopts a method for measuring T2 distribution, which has the advantages of high degree of automation, simple operation, short time and non-destructiveness on the core plunger sample, and is suitable for researching the pore structures of multiple core plunger samples. Specifically, the experimental instrument in the present application is a high-temperature and high-pressure nuclear magnetic resonance online test platform, and the experimental equipment is mainly composed of a nuclear magnetic resonance core analyzer, an ISCO pump, an annular pressure pump and a nonmetallic nonmagnetic core holder. The core holder is made of a PEEK (Polyether-ether-ketone) material, and can be used for nuclear magnetic resonance online measurement while meeting displacement. Preset annular pressure is applied to the core holder via an annular pressure system to simulate stratum pressure, and hydrogen-free perfluorinated hydrocarbon oil can be used as annular pressure fluid. The ISCO pump ensures that the fluid displaces the core in a constant flow state or a constant pressure state. A computer terminal performs tests of T2 relaxation time spectra and nuclear magnetic resonance imaging on the state of the rock on line via software, and records and saves experimental data.

For nuclear magnetic resonance, according to the nuclear magnetic resonance relaxation mechanism and the rock physical property measurement principle, under the condition that the rock saturated in water is in a uniform magnetic field, the nuclear magnetic resonance transverse relaxation time T2 is directly proportional to the pore throat radius $r_c$:

$$T_2 = \left(\frac{1}{\rho_2 \times F_S}\right) \times r_c$$

$$T_2 = C \times r_c$$

Wherein C is a conversion coefficient between $T_2$ and $r_c$, $\rho_2$ is transverse surface relaxation strength of the rock, is not affected by pressure and temperature and is a parameter related to rock properties and its unit is μm/ms, $F_S$ is a pore shape factor. Hence, after the value of C is determined, the distribution curve of the pore radius $r_c$ of the core plunger sample can be obtained by using nuclear magnetic resonance T2 spectra. The relaxation time spectra of the nuclear magnetic resonance transverse relaxation time T2 show the distribution of pores having different sizes, the relaxation time is directly proportional to the pore radius, and longer relaxation time represents larger pores. When the rock types of the core plunger samples are different, their nuclear magnetic resonance (NMR) characteristics are greatly different.

Further, in the present application, the specific process of establishing an identification plate includes:

Step 1: dividing pores of the core plunger sample according to the length of relaxation time in the normal pressure nuclear magnetic resonance test result, wherein the normal pressure nuclear magnetic resonance spectra having a relaxation time of more than 200 ms in the normal pressure nuclear magnetic resonance test result are divided into large pores of the core plunger sample, the normal pressure nuclear magnetic resonance spectra having a relaxation time of more than 20 ms and less than 200 ms in the normal pressure nuclear magnetic resonance test result are divided into medium pores of the core plunger sample, and the normal pressure nuclear magnetic resonance spectra having a relaxation time of less than 20 ms in the normal pressure nuclear magnetic resonance test result are divided into small pores of the core plunger sample;

Step 2: respectively calculating the percentages of the normal pressure nuclear magnetic resonance spectrum areas corresponding to the large pores, the medium pores and the small pores to the total area of the normal pressure nuclear magnetic resonance spectrum; and Step 3: respectively projecting the percentage of the normal pressure nuclear magnetic resonance spectrum area corresponding to the large pores to the total area of the normal pressure nuclear magnetic resonance spectrum, the percentage of the normal pressure nuclear magnetic resonance spectrum area corresponding to the medium pores to the total area of the normal pressure nuclear magnetic resonance spectrum and the percentage of the normal pressure nuclear magnetic resonance spectrum area corresponding to the small pores to the total area of the normal pressure nuclear magnetic resonance spectrum to a triangular plot plate to obtain the identification plate.

The present application will give a specific embodiment below to specify the process of establishing a nuclear magnetic resonance plate:

Step 1: for the core plunger sample i having the rock type A, dividing pores of the core plunger sample according to the length of relaxation time in the normal pressure nuclear magnetic resonance test result (T2 spectra), wherein the normal pressure nuclear magnetic resonance spectra having a relaxation time of more than 200 ms in the normal pressure nuclear magnetic resonance test result is divided into large pore of the core plunger sample, the normal pressure nuclear magnetic resonance spectra having a relaxation time of more than 20 ms and less than 200 ms in the normal pressure nuclear magnetic resonance test result is divided into medium pore of the core plunger sample, and the normal pressure nuclear magnetic resonance spectra having a relaxation time of less than 20 ms in the normal pressure nuclear magnetic resonance test result is divided into small pore of the core plunger sample.

Step 2: respectively calculating the percentage of the T2 spectrum area of the large pores to the total area, the percentage of the T2 spectrum area of the medium pores to the total area and the percentage of the T2 spectrum area of the small pores to the total area, the formulas being:

$$A_1 = \frac{S_1}{S_1 + S_2 + S_3} \times 100\%$$

$$A_2 = \frac{S_2}{S_1 + S_2 + S_3} \times 100\%$$

$$A_3 = \frac{S_3}{S_1 + S_2 + S_3} \times 100\%$$

wherein A1 is the percentage of small pores, A2 is the percentage of medium pores, A3 is the percentage of large pores, S1 is the T2 spectrum area of small pores, S2 is the T2 spectrum area of medium pores, S3 is the T2 spectrum area of large pores, and A1+A2+A3=1.

Therefore, a pore structure number, carrying the core plunger sample i identifier, of the nuclear magnetic resonance test is obtained. The rock type of the core plunger sample can be known according to the core plunger sample i identifier, and specifically, the pore structure number, corresponding to the core plunger sample i, of the nuclear magnetic resonance test is: (A1i, A2i, A3i).

Step 3: projecting (A1i, A2i, A3i) to a triangular plot plate to obtain the identification plate.

It should be noted that, when there are several core plunger samples and they have different rock types, a nuclear magnetic resonance identification plate of each rock type can be respectively obtained by using the above method.

For establishing a first relation, specifically:

for the measured T2 spectra of the completely saturated core plunger sample, the nuclear magnetic resonance signal strength can be converted into the porosity, and scaled by using the measured porosity. Specifically, the first relation is:

$$\Phi_{nmr} = C_\Phi \times \frac{A}{V_b} \times 100\%$$

wherein $\Phi_{nmr}$ is the porosity of the core plunger sample, $V_b$ is the volume of the core plunger sample, A is the total amplitude of nuclear magnetic resonance test echo signals, $C_\Phi$ is a scale factor between the porosity measured from the standard sample having known porosity and the porosity of nuclear magnetic resonance calculation, the scale factor is related to the rock type, and in the present application, each rock type has corresponding $C_\Phi$.

For establishing a second relation, specifically:

statistical analysis is performed by using the air permeability of the core plunger sample and the nuclear magnetic resonance measurement result, and the permeability of the core plunger sample is mainly calculated by adopting an SDR extension model. Specifically, the second relation is:

$$K_{nmr} = C_K \times \left(\frac{\Phi_{nmr}}{100}\right)^4 \times T_{2g}^2$$

wherein $K_{nmr}$ is the permeability of the core plunger sample and its unit is millidarcy ($10^{-3} \times \mu m^2$); $C_K$ is a scale factor between the permeability measured from the standard sample having known permeability and the permeability of nuclear magnetic resonance calculation, the scale factor is related to the rock type, in the present application, each rock type has corresponding $C_K$, $\Phi_{nmr}$ is the porosity of the core plunger sample, and $T_{2g}$ is a geometric mean of the nuclear magnetic resonance transverse relaxation time of the core plunger sample.

For establishing a third relation, specifically:

statistical analysis is performed by using the pore structure of the core plunger sample and the nuclear magnetic resonance measurement result, and the conversion coefficient between the pore structure distribution curve and the nuclear magnetic resonance transverse relaxation time (T2) is mainly determined by adopting a least square method. Specifically, the third relation is:

$$r_c = C_r \times T_2$$

wherein $T_2$ is the nuclear magnetic resonance transverse relaxation time, $r_c$ is the pore throat radius of the core plunger sample, $C_r$ is a conversion coefficient between the pore structure measured from the standard sample having known pore structure and the pore structure of nuclear magnetic resonance conversion, and the conversion coefficient is related to the rock type After step 106 is completed, step 107 is executed: based on the identification plate, the first relation, the second relation and the third relation, according to the normal pressure nuclear magnetic resonance test result of a target rock sample, characterizing the rock type, porosity, permeability and pore structure of the target rock sample under normal pressure.

Specifically, the target rock sample is a sample having the same rock type as the core plunger sample, in step 107, a normal pressure nuclear magnetic resonance test can be performed on the target rock sample first, and after a normal pressure nuclear magnetic resonance test result of the target rock sample is obtained, based on the identification plate, the first relation, the second relation and the third relation, according to the normal pressure nuclear magnetic resonance test result of the target rock sample, the rock type, porosity, permeability and pore structure of the target rock sample under normal pressure can be derived. Thus, the rock physical characteristics of the target rock sample under normal pressure can be directly obtained by adopting the method of the present application without thin section observation and rock physical characteristic test analysis, the obtained rock physical characteristics are accurate, the obtaining process is fast, and the purpose of massively, quickly and non-destructively measuring the rock physical characteristics of the sample is fulfilled.

After step 107 is completed, step 108 is executed: based on the identification plate, the first relation, the second relation and the third relation, according to an overburden pressure nuclear magnetic resonance test result of the target rock sample, characterizing the porosity, permeability and pore structure of the target rock sample under its buried depth.

Specifically, before the porosity, permeability and pore structure of the target rock sample under its buried depth are characterized, an overburden pressure nuclear magnetic resonance test is required for the target rock sample. In terms of the overburden pressure nuclear magnetic resonance, it is bound to cause compression or tension from one stress state to the other stress state according to the theory of rock mechanics, i.e., the rock is subjected to elastic or plastic deformation. Meanwhile, the deformation of the rock necessarily results in changes of the pore structure and pore volume of the rock. For example, with the increase of pressure, the rock has such changes as pore volume reduction, closure of pore throats and cracks and the like, which will greatly affect the seepage of fluid therein, and if the above-mentioned actual situation of the rock cannot be simulated by adopting the normal pressure nuclear magnetic resonance test, the actual rock physical characteristics of the sample under its buried depth cannot be learnt clearly. In the present application, an overburden pressure nuclear magnetic resonance test is performed on the target rock sample under a specified test pressure, the specified test pressure is a lithostatic pressure corresponding to the buried depth of the target rock sample, and the finally obtained test result can really and accurately reflect the rock physical characteristics of the sample under its buried depth.

The present application will give a specific test process of the overburden pressure nuclear magnetic resonance test applied to the core plunger sample below:

Step 1, saturating the core plunger sample with simulated stratum water solution and then putting the core plunger sample into a nonmagnetic core holder, and fixing the nonmagnetic core holder into a nuclear magnetic resonance coil;

Step 2, setting the confining pressure of the holder to be initial static stress, performing water flooding till the flow rate is stable, keeping the flow rate for over 50 minutes, and testing nuclear magnetic resonance T2 relaxation spectra; and Step 3 increasing the confining pressure of the holder for the core plunger sample to a lithostatic pressure corresponding to the buried depth of the target rock sample, performing water flooding till the flow rate is stable, keeping the flow rate for over 50 minutes, and testing nuclear magnetic resonance T2 relaxation spectra.

Further, after the overburden pressure nuclear magnetic resonance test result of the target rock sample is obtained, based on the identification plate, the first relation, the second relation and the third relation, according to the overburden pressure nuclear magnetic resonance test result of the target rock sample, the porosity, permeability and pore structure of the target rock sample under its buried depth can be derived. Therefore, the rock physical characteristics of the target rock sample under its buried depth can be massively, quickly, non-destructively and accurately obtained by adopting the method of the present application.

It should be noted that, in the present application, for step 105, the mercury-injection capillary pressure test will destroy the core plunger sample in a certain degree, so that the nuclear magnetic resonance test result is not ideal. Thus, the nuclear magnetic resonance test can be performed on the core plunger sample first, and then the mercury-injection capillary pressure test is performed on the core plunger sample after the nuclear magnetic resonance test is completed. In addition, the target rock sample, which is a sample for characterizing the rock physical characteristics, does not need porosity, permeability and mercury-injection capillary pressure tests.

One or more technical solutions in the embodiments of the present invention at least have the following technical effects or advantages:

In the present application, after a core plunger sample is extracted, a rock thin section corresponding to the core plunger sample is made, and the surface structure characteristics of the rock thin section are identified to determine the rock type of the rock thin section. The rock type of the rock thin section characterizes the rock type of the core plunger sample corresponding to the rock thin section. In the present application, after the core plunger sample is extracted, rock physical characteristic tests for measuring rock physical characteristics and a normal pressure nuclear magnetic resonance test are also performed on the core plunger sample to obtain rock physical characteristic test results and a normal pressure nuclear magnetic resonance test result of the core plunger sample. The rock physical characteristics include porosity, permeability and pore structure of the rock. Then, based on the rock type of the core plunger sample, the rock physical characteristic test results and the normal pressure nuclear magnetic resonance test result, an identification plate for characterizing the correspondence between the rock type and the nuclear magnetic resonance test result is established, a first relation for characterizing the correspondence between the porosity and the nuclear magnetic resonance test result is established, a second relation for characterizing the correspondence between the permeability and the nuclear magnetic resonance test result is established, and a third relation for characterizing the correspondence between the pore structure and the nuclear magnetic resonance result is established. Further, based on the identification plate, the first relation, the second relation and the third relation, according to the normal pressure nuclear magnetic resonance test result of the target rock sample, the rock type, porosity, permeability and pore structure of the target rock sample under normal pressure are characterized, and according to an overburden pressure nuclear magnetic resonance test result of the target rock sample, the porosity, permeability and pore structure of the target rock sample under its buried depth are characterized. Therefore, the rock physical characteristics of the target rock sample under the laboratory normal pressure environment and its buried depth are obtained massively, quickly, non-destructively and accurately, and a technical support is provided for oilfield evaluation on underground rock physical characteristics of each rock type.

Although the preferred embodiments of the present invention have been described, those skilled in the art could make additional alterations and modifications to these embodiments once they learn basic creative concepts. Therefore, the appended claims are intended to be interpreted as including the preferred embodiments and all the alterations and modifications falling into the scope of the present invention.

Obviously, those skilled in the art could make various alterations and modifications to the present invention without departing from the spirit and scope of the present invention. In this case, if these alterations and modifications of the present invention fall into the scope of the claims and equivalent technologies thereof, the present invention also intends to include these alterations and modifications.

The invention claimed is:

1. A method for characterizing rock physical characteristics of deeply buried carbonate rocks, comprising the following steps:
    determining a sampling position of the carbonate rocks;
    extracting a core plunger sample at the sampling position;
    making a rock thin section corresponding to the core plunger sample;
    determining a rock type of the rock thin section by identifying surface structure characteristics of the rock thin section, wherein the rock type of the rock thin section is used for characterizing the rock type of the core plunger sample corresponding to the rock thin section;
    performing a normal pressure nuclear magnetic resonance test and rock physical characteristic tests for measuring rock physical characteristics on the core plunger sample to obtain rock physical characteristic test results and a normal pressure nuclear magnetic resonance test result of the core plunger sample, wherein the rock physical characteristics comprise porosity, permeability and pore structure of the deeply buried carbonate rocks;
    based on the rock type of the core plunger sample, the rock physical characteristic test results and the normal pressure nuclear magnetic resonance test result, establishing an identification plate for characterizing the correspondence between the rock type and the nuclear magnetic resonance test result, establishing a first relation for characterizing the correspondence between the porosity and the nuclear magnetic resonance test result, establishing a second relation for characterizing the correspondence between the permeability and the nuclear magnetic resonance test result, and establishing a third relation for characterizing the correspondence between the pore structure and the nuclear magnetic resonance result;
    based on the identification plate, the first relation, the second relation and the third relation, according to the normal pressure nuclear magnetic resonance test result of a target rock sample, characterizing the rock type, porosity, permeability and pore structure of the target rock sample under normal pressure; and
    based on the identification plate, the first relation, the second relation and the third relation, according to an overburden pressure nuclear magnetic resonance test result of the target rock sample, characterizing the porosity, permeability and pore structure of the target rock sample under its buried depth.

2. The method of claim 1, wherein the sampling position comprises a carbonate segment without vugs and caves developing, a semi-filled crack developed segment and a full-filing crack developed segment, the rock type of the sampling position is uniform, and the rock thickness of the sampling position is more than 30 cm.

3. The method of claim 1, wherein the height of the core plunger sample is 3.0-6.0 cm.

4. The method of claim 1, wherein the surface structure characteristics comprise at least one of carbonate grain characteristic, carbonate mud characteristic, biological framework characteristic, carbonate crystalline characteristic and crack characteristic, and the rock type is mudstone, wackestone, packstone, grainstone, boundstone, crystalline carbonates, semi-filled crack carbonate rock or full-filled crack carbonate rock.

5. The method of claim 1, wherein the step of performing the rock physical characteristic tests on the core plunger sample comprise:
performing a porosity test, a permeability test and a mercury-injection capillary pressure test on the core plunger sample.

6. The method of claim 1, wherein before the step of characterizing the porosity, permeability and pore structure of the target rock sample under its buried depth, the method further comprises the following step:
performing an overburden pressure nuclear magnetic resonance test on the target rock sample to obtain an overburden pressure nuclear magnetic resonance test result of the target rock sample;
wherein the step of performing the overburden pressure nuclear magnetic resonance test on the target rock sample comprises:
performing a nuclear magnetic resonance test on the target rock sample under a specified test pressure, wherein the specified test pressure is lithostatic pressure corresponding to the buried depth of the target rock sample.

7. The method of claim 1, wherein the step of establishing the identification plate for characterizing the correspondence between the rock type and the nuclear magnetic resonance test result comprises:
dividing pores of the core plunger sample according to the length of relaxation time in the normal pressure nuclear magnetic resonance test result, wherein normal pressure nuclear magnetic resonance spectra having a relaxation time of more than 200 ms in the normal pressure nuclear magnetic resonance test result are divided into large pores of the core plunger sample, the normal pressure nuclear magnetic resonance spectra having a relaxation time of more than 20 ms and less than 200 ms in the normal pressure nuclear magnetic resonance test result are divided into medium pores of the core plunger sample, and the normal pressure nuclear magnetic resonance spectra having a relaxation time of less than 20 ms in the normal pressure nuclear magnetic resonance test result are divided into small pores of the core plunger sample;
respectively calculating percentages of the normal pressure nuclear magnetic resonance spectrum areas corresponding to the large pores, the medium pores and the small pores to the total area of the normal pressure nuclear magnetic resonance spectrum; and
respectively projecting the percentage of the normal pressure nuclear magnetic resonance spectrum area corresponding to the large pores to the total area of the normal pressure nuclear magnetic resonance spectrum, the percentage of the normal pressure nuclear magnetic resonance spectrum area corresponding to the medium pores to the total area of the normal pressure nuclear magnetic resonance spectrum and the percentage of the normal pressure nuclear magnetic resonance spectrum area corresponding to the small pores to the total area of the normal pressure nuclear magnetic resonance spectrum to a triangular plot plate to obtain the identification plate.

8. The method of claim 1, wherein the first relation is:

$$\Phi_{nmr} = C_\Phi \times \frac{A}{V_b} \times 100\%$$

wherein $\Phi_{nmr}$ is the porosity of the core plunger sample, $V_b$ is the volume of the core plunger sample, A is the total amplitude of nuclear magnetic resonance test echo signals, and $C_\Phi$ is a scale factor between the porosity measured from a standard sample having known porosity and the porosity of nuclear magnetic resonance calculation.

9. The method of claim 1, wherein the second relation is:

$$K_{nmr} = C_K \times \left(\frac{\Phi_{nmr}}{100}\right)^4 \times T_{2g}^2$$

wherein $K_{nmr}$ is the permeability of the core plunger sample, $C_K$ is a scale factor between the permeability measured from the standard sample having known permeability and the permeability of nuclear magnetic resonance calculation, $\Phi_{nmr}$ is the porosity of the core plunger sample, and $T_{2g}$ is a geometric mean of the nuclear magnetic resonance transverse relaxation time of the core plunger sample.

10. The method of claim 1, wherein the third relation is:

$$r_c = C_r \times T_2$$

wherein $r_c$ is the pore throat radius of the core plunger sample, $T_2$ is the nuclear magnetic resonance transverse relaxation time, and $C_r$ is a conversion coefficient between the pore structure measured from the standard sample having known pore structure and the pore structure of nuclear magnetic resonance conversion.

* * * * *